(12) United States Patent
Durbin et al.

(10) Patent No.: US 7,118,375 B2
(45) Date of Patent: Oct. 10, 2006

(54) METHOD AND SYSTEM FOR DENTAL MODEL OCCLUSAL DETERMINATION USING A REPLICATE BITE REGISTRATION IMPRESSION

(76) Inventors: Duane Milford Durbin, 7660 Norcanyon Way, San Diego, CA (US) 92126; Dennis Arthur Durbin, 711 Marsolan, Solana Beach, CA (US) 92075

( * ) Notice: Subject to any disclaimer, the term of this patent is extended or adjusted under 35 U.S.C. 154(b) by 449 days.

(21) Appl. No.: 10/753,226

(22) Filed: Jan. 8, 2004

(65) Prior Publication Data

US 2005/0153257 A1    Jul. 14, 2005

(51) Int. Cl.
*A61C 19/04*    (2006.01)

(52) U.S. Cl. .................. 433/68; 433/71; 433/213; 433/214

(58) Field of Classification Search .................. 433/24, 433/68, 74, 213, 214
See application file for complete search history.

(56) References Cited

U.S. PATENT DOCUMENTS

| | | | |
|---|---|---|---|
| 3,349,489 A | | 10/1967 | Shackelford |
| 4,402,326 A | | 9/1983 | Okano et al. |
| 4,521,186 A | | 6/1985 | Wodlinger et al. |
| 4,575,805 A | * | 3/1986 | Moermann et al. .......... 700/163 |
| 4,611,288 A | * | 9/1986 | Duret et al. ................. 700/163 |
| 4,734,034 A | | 3/1988 | Maness et al. |
| 4,856,993 A | | 8/1989 | Maness et al. |
| 4,935,635 A | * | 6/1990 | O'Harra ................. 250/559.06 |
| 5,028,232 A | | 7/1991 | Snow |
| 5,338,198 A | * | 8/1994 | Wu et al. .................... 433/213 |
| 5,359,511 A | * | 10/1994 | Schroeder et al. ............ 433/75 |
| 5,372,502 A | * | 12/1994 | Massen et al. .............. 433/215 |
| 5,587,912 A | * | 12/1996 | Andersson et al. ........... 700/98 |
| 6,152,730 A | * | 11/2000 | Wildman ..................... 433/68 |
| 6,152,731 A | * | 11/2000 | Jordan et al. ................. 433/69 |
| 6,217,334 B1 | * | 4/2001 | Hultgren .................... 433/215 |
| 6,322,359 B1 | * | 11/2001 | Jordan et al. .................. 433/73 |
| 6,334,853 B1 | | 1/2002 | Kopelman et al. |
| 6,364,660 B1 | * | 4/2002 | Durbin et al. ................ 433/29 |
| 6,488,638 B1 | * | 12/2002 | Mushabac ................... 600/590 |
| 6,621,491 B1 | * | 9/2003 | Baumrind et al. .......... 345/419 |
| 6,648,640 B1 | * | 11/2003 | Rubbert et al. ............... 433/24 |
| 6,664,986 B1 | * | 12/2003 | Kopelman et al. .......... 715/849 |
| 2003/0064345 A1 | * | 4/2003 | Chishti et al. ................ 433/24 |

\* cited by examiner

*Primary Examiner*—Carry E. O'Connor
*Assistant Examiner*—Patrick J. Kilkenny

(57) ABSTRACT

Systems and methods for imaging a dental occlusal registration impression; developing a digital 3D surface contour model of the occlusal registration impression from the image data; electronically transferring the data representing the digital 3D surface contour model of the occlusal registration impression; fabricating a physical replicate of the occlusal registration impression; correlating features on upper and lower jaw dental models with features on the replicate occlusal registration impression model; and determining occlusal alignment of the upper and lower jaw dental models using the replicate occlusal registration impression model.

20 Claims, 14 Drawing Sheets

METHOD AND SYSTEM FOR DENTAL MODEL OCCLUSAL DETERMINATION USING A REPLICATE BITE REGISTRATION IMPRESSION

1. FIELD OF INVENTION

The present invention relates to methods and systems for determining occlusal alignment of upper and lower jaw dental models.

2. BACKGROUND

In many dental applications, a working model of a patient's teeth is needed that faithfully reproduces the patient's teeth and other dental structures, including the jaw structure. The model is typically created by first taking an impression of both the upper and lower jaws using an impression material such as alginate or polyvinylsiloxane (PVS). Once the impressions have set, a plaster or stone compound is poured into each of the impression trays to create the dental models for both the upper and lower jaws. Because the physical models are generally made using a separate impression tray for the upper and lower jaw impressions there is not an absolute way of determining the complete jaw alignment using only the cast upper and lower jaw models.

Conventionally, to determine the proper occlusal relationship between the teeth on the upper and lower jaws, a wax bite registration impression is taken. In determining bite registration a common approach typically conforms a sheet of wax to an arch shape and positions the wax intra-orally between a patient's upper and lower dental arches. For example, a wax bite can be obtained by inserting a thin sheet of wax into the patient's mouth and having them bite down on the wax thus leaving a bite mark on both sides of the wax sheet.

As an alternative to wax sheets a material such as a quick setting impression paste may be applied to both sides of a thin mesh and the coated mesh then placed into the patient's month whereupon the patient is asked to bite down on the coated mesh. Once the coating material becomes firm, the coated mesh with the bite registration impression is removed from the month.

The dentist or dental laboratory can then use the bite registration impression to align the cast of the upper jaw dental model into its bite impression marks while also aligning the cast of the lower jaw dental model into its corresponding bite impression marks on the opposing side of bite registration impression. With both cast jaw dental models aligned in their corresponding bite impression marks, the dentist or dental laboratory technician can directly view the correct full occlusion position of the jaws and teeth.

This alignment technique may be used to place corresponding marks or surfaces on the upper and lower jaw models to facilitate viewing the aligned models at a future time without the need to re-align with the bite registration impression. Alternatively, the alignment technique using the bite registration impression may also be used to position the upper and lower jaw castings for mounting in an articulator jig. After installation in the articulator jig, the proper alignment of the upper and lower jaw models may be rechecked using the bite registration impression.

While wax sheets or impression material coated meshes are commonly used for bite registration impressions, potential problems with these bite impressions includes the propensity for the impressions to warp, bend, distort and/or become brittle, depending on how the impression is handled, stored, and used. If the bite impression is compromised or lost, the patient's dentist or dental provider may need to retake the entire set of measurement and the patient's treatment may need to be completely revised based on the retake. In addition, the bite impression must be shipped to the dental laboratory for use in aligning the upper and lower jaw dental model castings. This requirement to ship the relatively fragile bite impression adds cost and time to the treatment process and increases the risk that the bite impression may be damaged or lost.

Systems which focus on taking occlusion measurements electronically have been developed to provide a diagnostic tool for occlusal analysis. U.S. Pat. No. 3,349,489 titled MULTIPLE CELLED PRESSURE SENSITIVE DENTAL DEVICE FOR MEASURING RELATIVE OCCLUSAL PRESSURES by John Shackelford discloses a pressure sensitive device adapted to be positioned between the teeth of a patient with flanges which engage the lingual and buccal sides of the teeth to aid in placing the and holding the device during a test bite. During a test bite, the pressure sensor output may be read from a meter that indicates the relative location of the patient's dental occlusions.

U.S. Pat. No. 4,402,326 titled OCCLUSION PRESSURE IMAGE SYSTEM by Michiaki Okano et. al. discloses an occlusion pressure sensor and an image display system that provides a visual display of occlusal pressure in the form of a black-and-white or color brilliance image on a CRT display.

U.S. Pat. No. 4,521,186 titled SYSTEM FOR DETERMINING THE FIRST PREMATURITY CONTACT OF DENTAL OCCLUSION by Harold Wodlinger et. al. discloses a system for determining the first dental occlusion prematurity. The disclosed system is comprised of an intra-oral sensor with embedded electrical contacts and a liquid crystal display that indicates the location of the occlusion prematurity relative to the edges of the intra-oral sensor.

U.S. Pat. No. 4,856,993 titled PRESSURE AND CONTACT SENSOR SYSTEM FOR MEASURING DENTAL OCCLUSION by William L. Maness et. al. discloses a method and apparatus for using a contact sensor for measuring the force between dental contact points as the jaw is closed on the sensor surface A commercial system is available that uses this technology to measure both biting time profiles and forces and thereby provides a graphical indication of the patient's occlusal force deviation from a "normal" occlusal force balance.

The electronics based dental occlusion measuring systems disclosed in the above U.S. patents are limited for use in aligning the physical jaw dental models in that while they do provide a visual indication of the two-dimensional occlusion contact points, this information is not readily usable by a dentist or dental laboratory technician to quickly orient and align the contact surfaces of the three-dimensional upper and lower jaw dental models. Further, the displayed visual information on the occlusal contacts is generally not available at the dental laboratory where the jaw models are fabricated and the occlusion alignment of the jaw dental models is performed.

U.S. Pat. No. 6,364,660B1 titled METHOD AND SYSTEM FOR IMAGING AND MODELING DENTAL STRUCTURES by Durbin et. al discloses a method and apparatus for mapping the structure and topography of dental formations such as periodontium and teeth, both intact and prepared, for diagnosis and dental prosthetics and bridgework by using an intra-oral image scanning technique.

When digital three-dimensional (3D) models of the upper and lower jaws are created, by utilizing such an intra oral scanning system, the bite registration of the upper and lower jaws is not measured since the scanning takes place with the jaws partially open. A method of obtaining a digital representation of the occlusal bite registration that can be transferred to a dental laboratory for use in fabricating a replicate bite registration impression model for determining the occlusal alignment of the upper and lower jaw dental models is now addressed.

SUMMARY

In one aspect, a method for creating a 3D surface contour model from a bite registration impression; a method for electronically transferring the bite registration impression 3D surface contour model data; a method for fabricating a physical replicate model of the bite registration impression using the 3D surface contour model data; and a method of using the replicate model of the bite registration impression to determine the occlusal alignment between the upper and lower jaws of dental models.

Implementations of the above aspect may include one or more of the following: The bite registration impression can be used to obtain a partial occlusion or a full occlusion. The bite registration impression may be taken with the jaws closed or partially closed. The jaw dental models requiring bite registration alignment can represent partial jaws or full jaws. The jaw dental models requiring bite registration alignment may be dental stone castings made from conventional impressions such as jaw impressions taken using alginate or PVS impression materials. Alternatively, the jaw dental models requiring bite registration alignment may be fabricated from digital 3D model data using numerical controlled machining or rapid prototyping equipment such as Stereo Lithographic Apparatus (SLA), Objet Polyjet (OBJ), Fused Deposition Modeling (FDM), Selective Laser Sintering (SLS) or Three Dimensional Printing (3DP) equipment. A digital 3D surface contour model may be constructed for the bite registration impression. The digital 3D surface model of the bite registration impression may be transferred electronically using means such as a modem or the internet. The digital 3D surface contour model of the bite registration impression may be used to fabricate a physical replicate of the bite registration impression using numerically controlled machining or rapid prototyping equipment such as Stereo Lithographic Apparatus (SLA), Objet Polyjet (OBJ), Fused Deposition Modeling (FDM), Selective Laser Sintering (SLS) or Three Dimensional Printing (3DP) equipment. The physical replicate made from the digital model of the bite registration impression may be a full replicate or it may be a partial replicate of the original bite registration impression.

In another aspect, a system for imaging the surfaces of a bite registration impression and using the imaging data to construct a digital 3D surface contour model of the bite registration impression, a means for displaying the 3D surface contour model of the imaged bite registration impression, a means to transfer the 3D surface contour model data over a network and a means to convert the 3D surface contour model data to a format that accommodates the fabrication of a physical replicate of the bite registration impression 3D surface contour model using numerically controlled machining or rapid prototyping equipment.

Advantages of the system may include one or more of the following. The invention captures a digital three-dimensional (3D) surface contour model of an occlusal (bite) registration impression for use in the determination of the correct positioning of the upper and lower jaws for physical dental models. The system enables the dentist or dental laboratory to use the 3D surface contour models to quickly and easily create high-quality and durable replicate bite registration impressions for use in aligning the bite registration of the upper and lower jaw dental models. The physical replicates of the digital bite registration impression when used in conjunction with dental models of the upper and lower jaw would have application in dental diagnosis and for the specification and manufacture of dental prosthetics such as bridgeworks, crowns or other precision moldings and fabrications. In addition, it would have utility in the diagnosis and treatment planning process for dental malocclusions. The system would allow the data representing a bite registration impression 3D surface contour model to be transmitted electronically to support activity such as professional consults, insurance provider reviews, and the remote fabrication of replicate bite registration impression models. The bite registration impression 3D surface contour model may be electronically archived for future reference or to use for fabricating multiple replicates of the original bite registration impression.

The system automatically digitizes and develops a 3D surface contour model of the bite registration impression, and displays the information for review, therefore ensuring a higher quality result. The system eliminates the time consuming step of shipping the physical bite registration impression to a dental laboratory. The system eliminates the risk that a physical bite registration impression is damaged by handling or shipment and that use of the damaged impression compromises the treatment result. If a replicate bite registration impression model is damaged or lost, additional replicate models may be fabricated from the archived data file for the digital 3D bite registration surface contour model.

The foregoing, along with further features, advantages, and benefits of the invention, will be seen in the following detailed description of a presently preferred embodiment representing the best mode contemplated at this time for carrying out the invention. The description will refer to accompanying drawings as follows.

DETAILED DESCRIPTION

Figure 1:
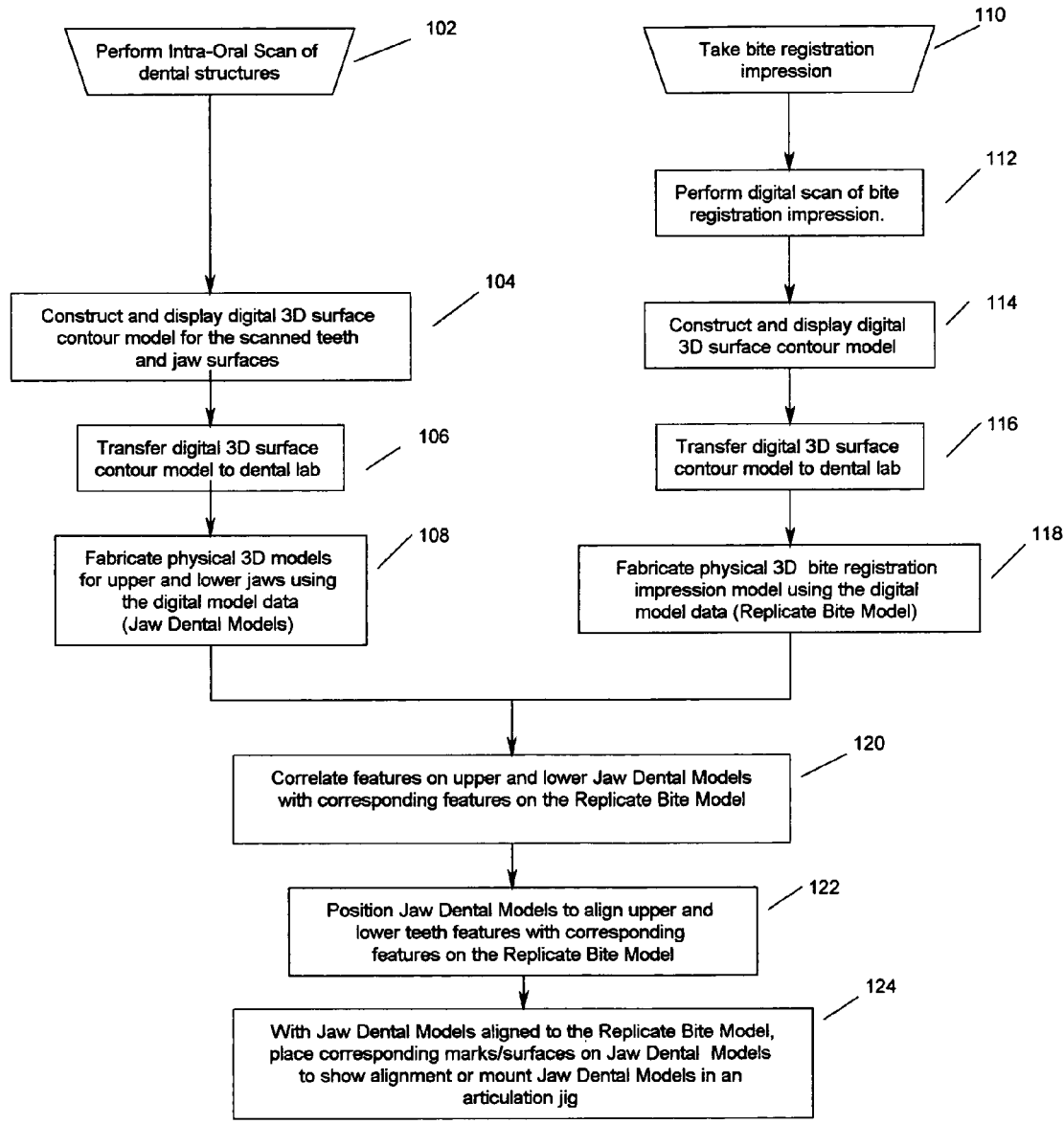
FIG. 1 shows one embodiment of a process utilizing dental models derived from a an intra-oral digital scan and a replicate bite registration impression model to determine occlusal registration between the upper and lower jaw dental models.

Referring to FIG. 1, one embodiment utilizes dental models fabricated from digital 3D dental models and a replicate bite registration impression model to determine the occlusal alignment of the upper and lower jaw dental models. First, an intra-oral scan of a dental structure is taken (step 102), and a 3D model of the upper and lower jaws is constructed (step 104). The digital 3D surface contour model of the scanned jaw surfaces is transferred to a dental laboratory (step 106). The 3D surface contour model data is used to fabricate full upper and lower jaw or partial upper and lower jaw physical replicates of the digital 3D jaw models (step 108).

In parallel or in seriatim, a bite registration impression is performed (step 110), the bite registration impression is digitally scanned (step 112) and a 3D model of the surface contour of the bite registration impression is created from the digital scan data (step 114). The digital 3D surface contour model of the scanned bite registration impression surfaces is transferred to a dental laboratory (step 116). The 3D surface contour model data is used to fabricate a physical replicate of the digital 3D bite registration model (step 118).

Using the physical replicates from steps 108 and 118, features on the upper and lower jaw dental models are correlated with corresponding features on the replicate bite model (step 120). Using the correlated features between the physical models to determine the general alignment, the replicate bite model is positioned between the upper and lower jaw dental models and the upper jaw dental model is positioned such that the upper jaw dental model surfaces are nested into the corresponding surfaces of the upper side of the replicate bite model while at the same time the lower jaw dental model is positioned such that the lower jaw dental model surfaces are nested into the corresponding surfaces of the lower side of the replicate bite model (step 122).

With the upper and lower jaw dental models nested into the replicate bite model, the alignment of the upper jaw dental model (FIG. 3) with the lower jaw dental model (FIG. 4) is now complete and the occlusal alignment of the jaw dental models is directly viewed. Corresponding marks or surfaces may be placed on the jaw dental models to show occlusal alignment or the jaw models may be mounted into an articulation jig (step 124).

Figure 2:
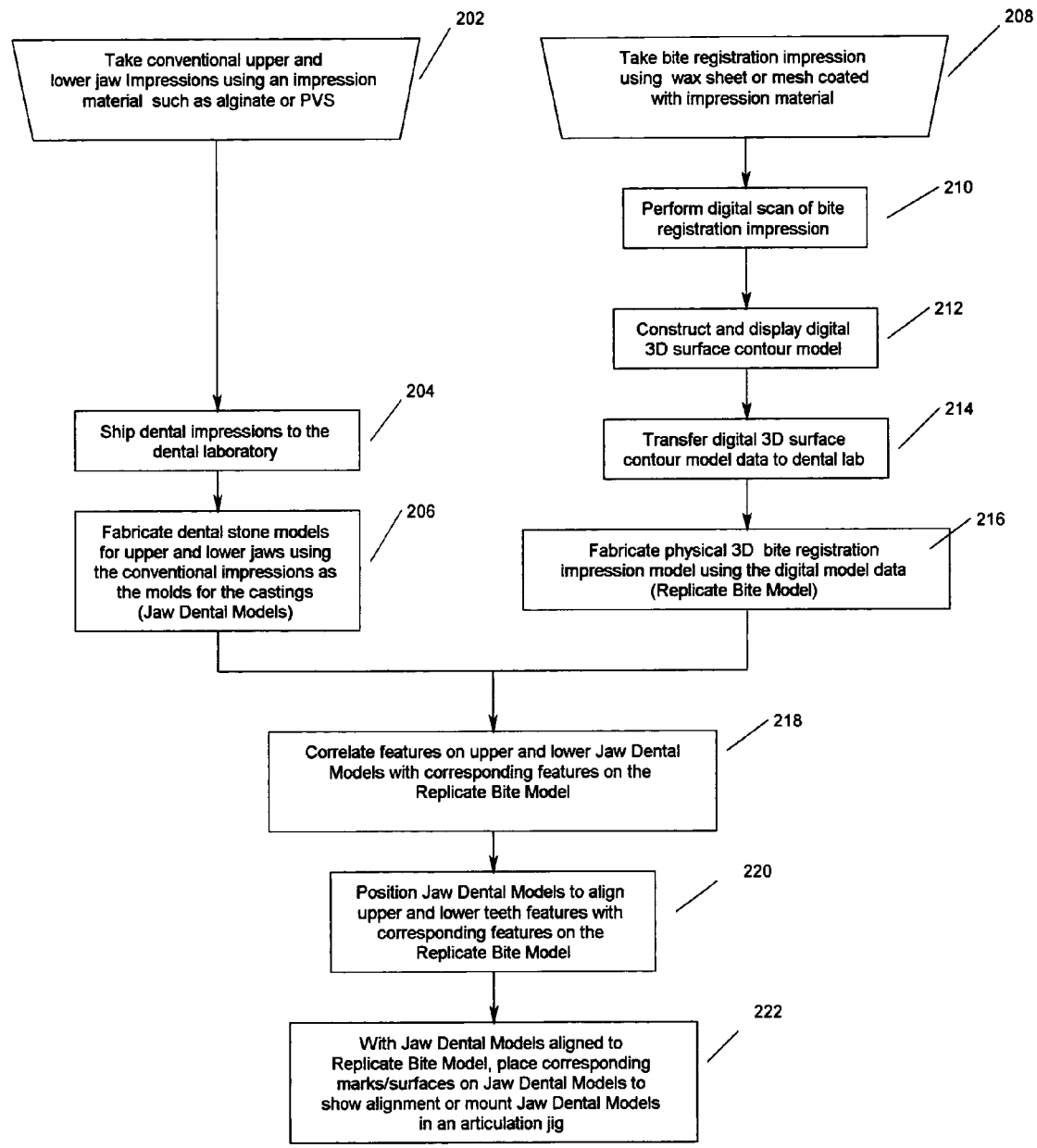
FIG. 2 shows a second embodiment of a process utilizing dental models derived from dental stone castings taken from conventional impressions and a replicate bite registration impression model to determine bite registration between the upper and lower jaw dental models.

Referring to FIG. 2, a second embodiment utilizes dental models fabricated from dental stone castings made from conventional upper and lower jaw, full or partial jaw impressions, and a replicate bite registration impression model to determine the occlusal alignment of the upper and lower jaw dental models. First, conventional full or partial, upper and lower jaw impressions are taken using an impression material such as alginate or polyvinylsiloxane (PVS) (step 202). The impressions are then shipped to a dental laboratory (step 204) where the impressions are used as the molds for casting dental stone models of the upper and lower jaw surfaces (step 206).

In parallel or in seriatim, a bite registration impression is performed (step 208), the bite registration impression is digitally scanned (step 210) and a 3D model of the surface contour of the bite registration impression is created from the digital scan data (step 212). The digital 3D surface contour model of the scanned bite registration impression surfaces is transferred to a dental laboratory (step 214). The 3D surface contour model data is used to fabricate a physical replicate of the digital 3D bite registration impression model (step 216).

Using the cast jaw dental models from step 206 and the replicate bite model from step 216, features on the upper and lower jaw dental models are correlated with corresponding features on the replicate bite model (step 218). Using the correlated features between the physical models to determine the general alignment, the replicate bite model is positioned between the upper and lower jaw dental models and the upper jaw dental model is positioned such that the upper jaw dental model surfaces are nested into the corresponding surfaces of the upper side of the replicate bite model while at the same time the lower jaw dental model is positioned such that the lower jaw model surfaces are nested into the corresponding surfaces of the lower side of the replicate bite model (step 220).

With the upper and lower jaw dental models nested into the replicate bite model, the alignment of the upper jaw dental model (FIG. 3) with the lower jaw dental model (FIG. 4) is now complete and the occlusal alignment of the jaw dental models is directly viewed. Corresponding marks or surfaces may be placed on the jaw dental models to show occlusal alignment or the jaw models may be mounted into an articulation jig (step 222).

Figure 3:
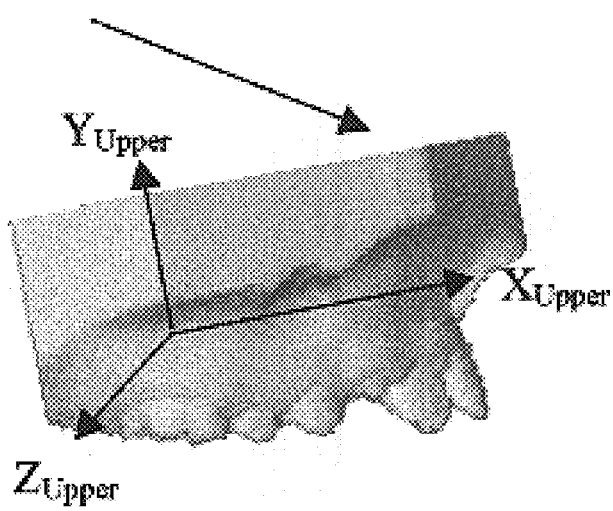
FIG. 3 and FIG. 4 show exemplary dental models of the upper and lower jaws created either from digital scans of each jaw or from dental stone castings taken from conventional impressions with the jaw in an open position.
Figure 4:
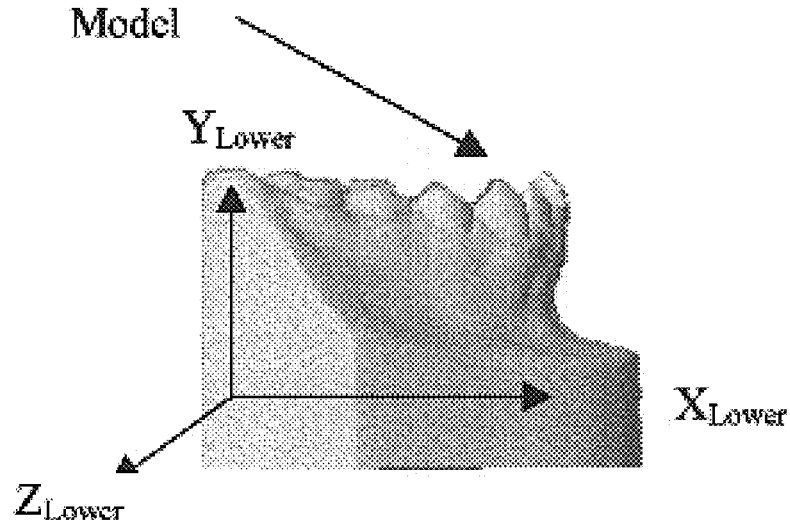

Referring to FIG. 3 and FIG. 4, one embodiment of this invention utilizes digital 3D dental models of the upper jaw (FIG. 3) and lower jaw (FIG. 4) created from separate scans of each jaw with the jaw in an open position. The digital 3D dental models (FIG. 3 and FIG. 4) are acquired by use of an intra oral scanner that captures and processes images of the dental structures and generates a 3D surface contour of the scanned structures. Typically the scanned structures include both the anterior and posterior teeth surfaces and a region of gingiva adjacent to the base of the teeth. The upper jaw scan may also include the palate.

The surface contours of the 3D models (FIGS. 3 and 4) are defined by a matrix of points, and for a Cartesian coordinate system, the x, y and z value assigned to the point represents a location that is on the surface contour of the scanned dental structure. As shown in FIGS. 3 and 4, the coordinate reference frame for the upper jaw model and the lower jaw model are typically in an arbitrary and unknown alignment with respect to each other. This difference in the coordinate reference frame alignment reflects that the upper and lower jaw 3D models were obtained independently and in each case the jaw was sufficiently open to provide the intra-oral scanner with access to the posterior surfaces of the dental structures.

Figure 5:
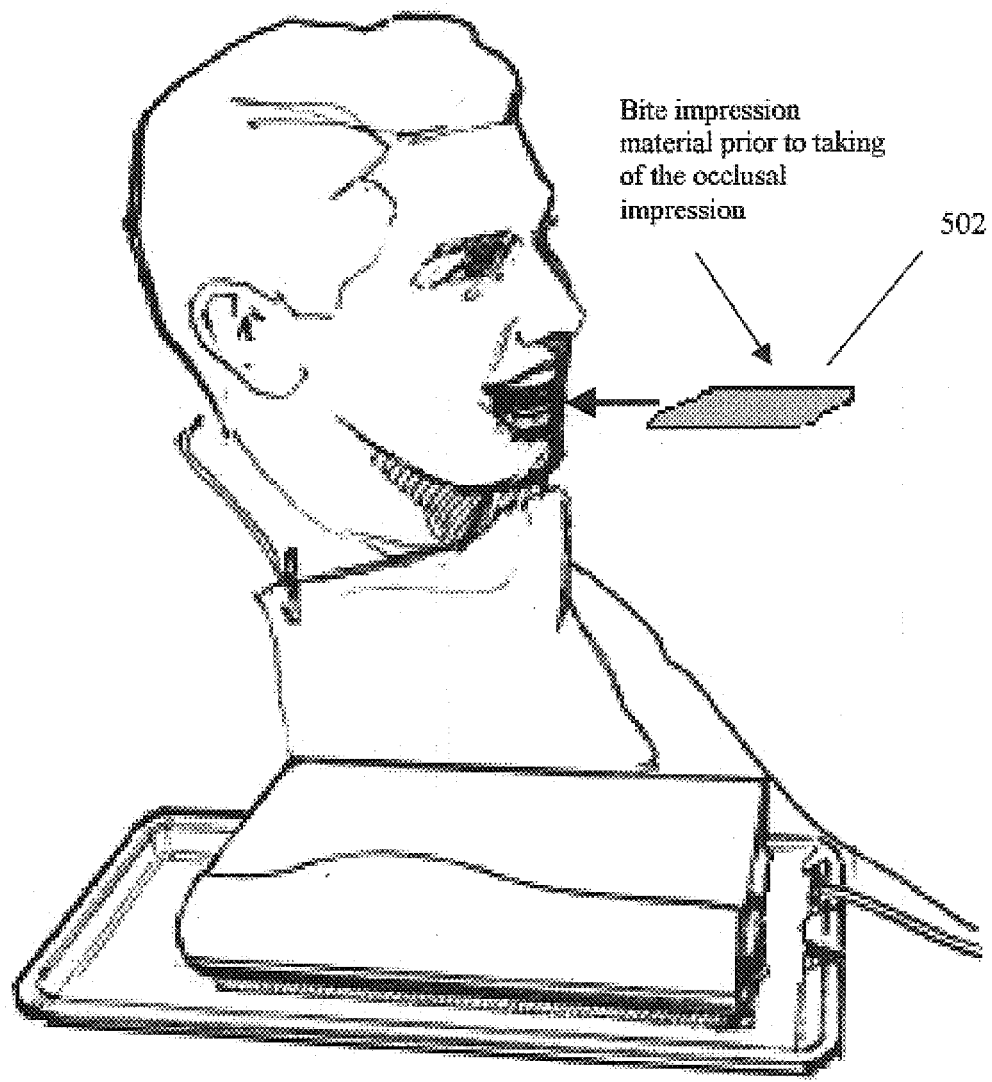
FIG. 5 shows the process of inserting a fresh sheet of bite registration impression material between the upper and lower jaws of the patient.
Figure 6:
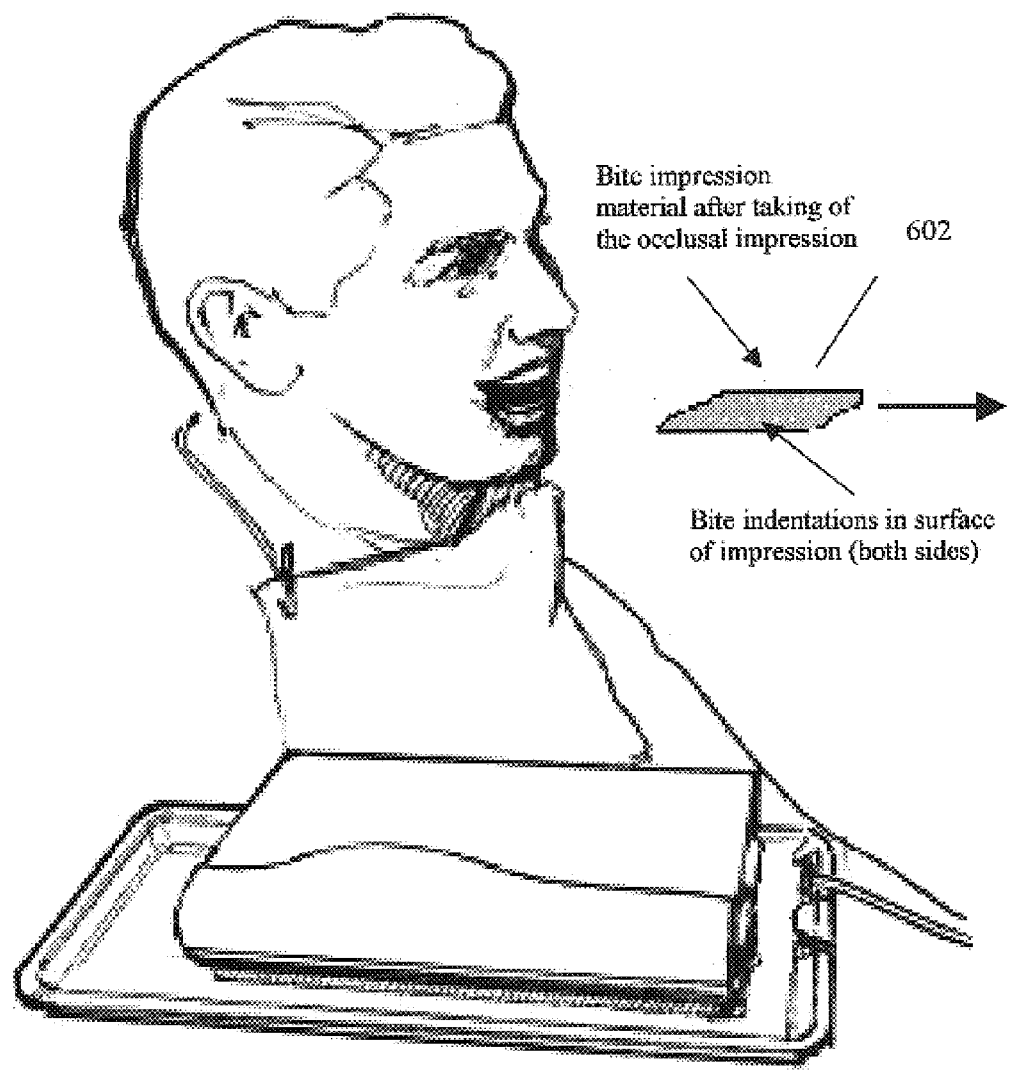
FIG. 6 shows the removal of the bite registration material from the patient, after the patient has bitten down on the material and created the bite surface indentations on both the upper and lower jaw sides of the bite registration material. This is commonly referred to as the bite registration impression.

To obtain an indication of the occlusal alignment between the upper and lower jaws a bite registration impression is typically taken with the jaws in a closed position. Referring to FIG. 5, the bite registration impression process may use a sheet of impression material 502 shaped in a fashion to fit between the teeth of the opened upper and lower jaws. Once the sheet of impression material is positioned between the open upper and lower jaws, the jaws are closed on the sheet of impression material and the occlusal surfaces of the upper and lower jaws are embedded into the impression material causing it to conform to the occlusal surface contours of the opposing jaw surfaces. Referring now to FIG. 6, the jaws are then opened and the bite registration impression 602 is removed. The indentations from the bite of the closed jaw are evidenced on both sides of the removed bite registration impression.

Figure 7:
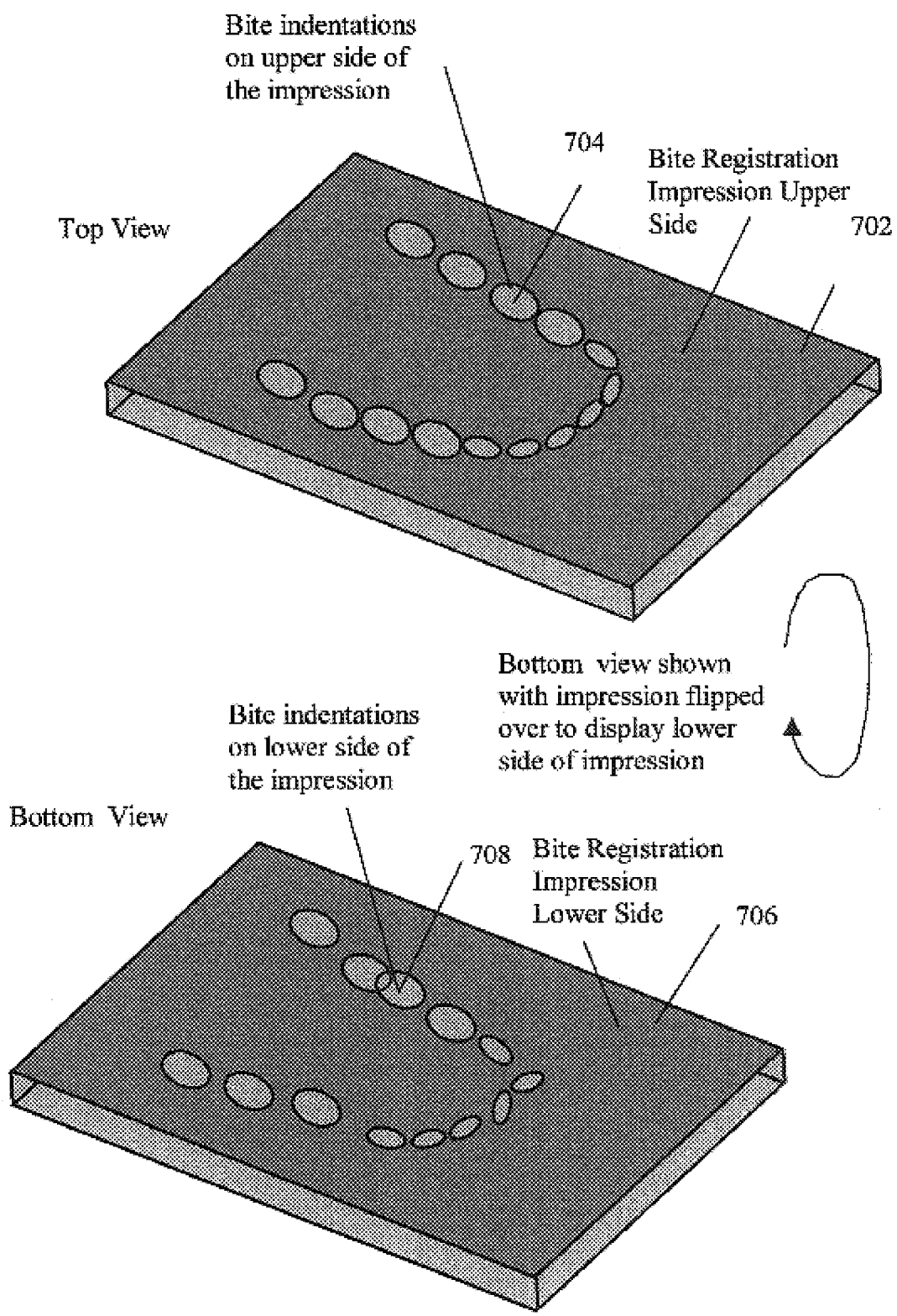
FIG. 7 shows the upper jaw side and the lower jaw side of the bite registration impression and illustrates the indentations made in the two surfaces of the bite registration material.

FIG. 7 illustrates that after the bite registration impression is taken, the upper side 702 of the sheet of impression material has captured the indentations 704 corresponding to the occlusal surface of the upper jaw, while the lower side 706 of the sheet of impression material has captured the indentations 708 corresponding to the occlusal surface of the lower jaw. In some cases, the occlusal contacts of one or both jaws are such that they may penetrate through the sheet of impression material and breakout on the opposing side.

While bite registration impressions are commonly taken using wax sheets, there are a number of alternative materials used for taking bite registration impressions. For example, a layer of paste-like impression material such as alginate or PVS may be coated to both sides of a mesh that is sized and shaped to be intra-orally placed between the upper and lower jaws with the jaws in an open position. The jaws are then closed on the soft impression material and the material is held in place between the closed jaws for a few moments until the material has catalyzed and firmed to form a relatively solid mold of the occlusal surfaces. The jaws are then opened and the solidified bite registration impression is removed from the mouth. Whether obtained from a sheet of wax or a matrix of mesh and impression material or other bite registration materials well known in the art, the result is a bite registration impression that captures the surface contours of the upper and lower jaw occlusal surfaces with the jaws in a closed or near closed position.

Figure 8:
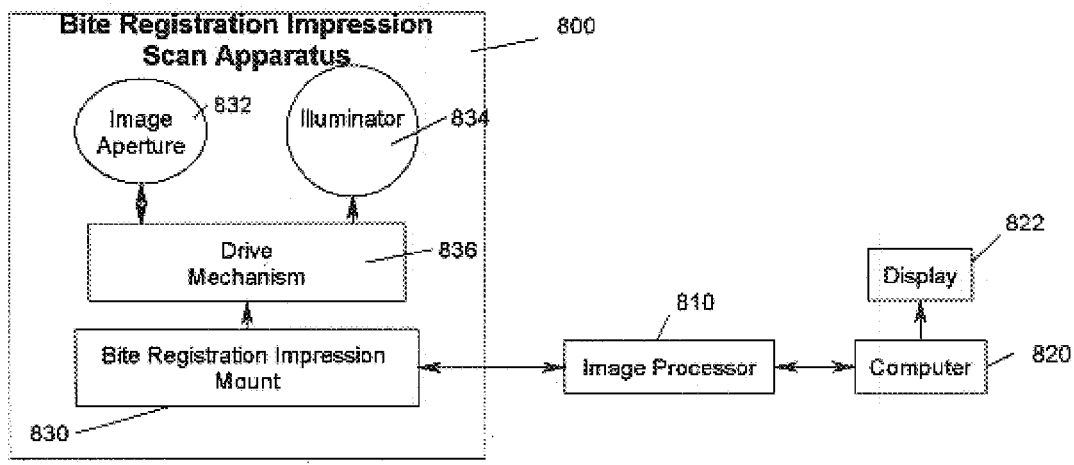
FIG. 8 illustrates an embodiment of a system for performing a scan of a bite registration impression and for generating a 3D surface contour model of the bite registration impression surfaces.

Referring to FIG. 8, a system block diagram depicting the instrumentation used in scanning the bite registration impression upper and lower surfaces and in generating 3D surface contour models, will facilitate a general understanding and appreciation of the disclosed method and apparatus.

In FIG. 8, a Bite Registration Impression Scan Apparatus 800, also referred to herein as the scanner, is adapted to image both sides of the bite registration impression. The scanner 800 captures images of the surface of the bite registration impression and communicates this information to an image processor 810. The image processor 810 in turn can communicate with a computer 820 and can display images of the scanned surfaces on a display 822 connected to the computer 820. Alternatively, functionalities of the computer 820 such as data storage and display can be provided directly by the image processor 810 in another embodiment. Images of the scanned bite registration impression and 3D surface contour models derived from the images can be transmitted as digital files to other equipment or locations by the computer 820.

In one implementation, the scanner 800 is integrated with a structure, such as a bite registration impression mount 830. An image aperture 832 is provided to capture images of the bite registration impression surfaces. The image aperture 832 can be an objective lens followed by relay lens in the form of a gradient indexed lens or a light-transmission cable such as a fiber optic cable to transmit images of the bite registration impression surfaces along a pre-selected distance to a camera. The fiber optic cable transmits light through small filamentary optical materials or fibers. Typically, the fibers include a central core and an outer surrounding cladding along the entire length of the fiber. The transmission of light through the fiber is based on the phenomenon of total internal reflection. For total internal reflection, the refractive index of the core is greater than the refractive index of the cladding. In one embodiment, optical fibers for the transmission of images comprised of visible through mid-infrared light can be used.

The output of the image aperture 832 can be provided to one or more sensors for detecting and converting incident light (photons from the light source reflected off the bite registration impression surface)—first into electronic charge (electrons) and, ultimately into digital bits. In one implementation, the output of the image aperture 832 is provided to a camera (not shown), which can be analog or digital. In one embodiment, the camera contains one or more image sensor(s) used to create digital images of the bite registration impression surface. These sensors can be devices such as a charge-coupled device (CCD) sensor or a complementary metal oxide semiconductor (CMOS) image sensor. The image sensor can be an array of individual photosensitive cells (pixels) whose size determines the limiting resolution. Image sensor arrays can have from 16×16 pixels to more than 1024×1024 pixels, and the arrays can be symmetrical or asymmetrical.

Further, a source of light delivered through an illuminator 834 is provided to illuminate the bite registration impression surfaces to improve the quality or contrast of the images taken by the image aperture 832. The light can be white light, light shown in one or more colors, or can come from a laser beam. The intensity of the light source used to illuminate the bite registration impression surfaces is ideally controllable and is in the frequency range of visible or infra-red light. In one embodiment, the light source can be integral to the bite registration impression mount 830. In another embodiment, light can be routed from the light source to the illuminator 834 by one or more fiber optic cables (not shown). This bundle of optical fibers can be positioned to surround the outer circumference of the image aperture 832 to create a plurality of illuminators. The field of illumination may be greater than the field of view of the image aperture 832 and may range up to 180 degrees. In another embodiment, the field of illumination may be a focused beam that illuminates a spot on the bite registration impression surface with an illumination spot size of dimensions less than 5 mm.

A drive mechanism 836 is provided to incrementally or continuously change the relative position of the image aperture 832 and the illuminator 834 with respect to the surfaces of the bite registration impression being scanned. In one embodiment, the image aperture 832 and the illuminator 834 are movably mounted on a track that is driven by the drive mechanism 836. The track can be a U-shaped track conforming to the outer dimensions of the bite registration impression's upper and lower surfaces. The drive mechanism 836 can be electrically actuated to move the image aperture 832 and the illuminator 834 in a manner that completely scans and captures images of both the upper and lower surfaces of the bite registration impression. Any of a variety of drive motors can be used, and the power of the motor through the drive mechanism 836 can be translated into motion for the image aperture 832 and the illuminator 834 through rotary, linear, hydraulic, or pneumatic mechanisms for example.

In an alternative embodiment of the drive mechanism, the bite registration impression mount 830 is movably coupled to the drive mechanism 836 while the image aperture 832 and illuminator 834 remain in a fixed position. The drive mechanism 836 can be electrically actuated to move the bite registration impression mount 830 in a manner that positions the bite registration impression surfaces with respect to the image aperture and illuminator such that both the upper and lower surfaces of the bite registration impression are completely scanned.

Figure 9:
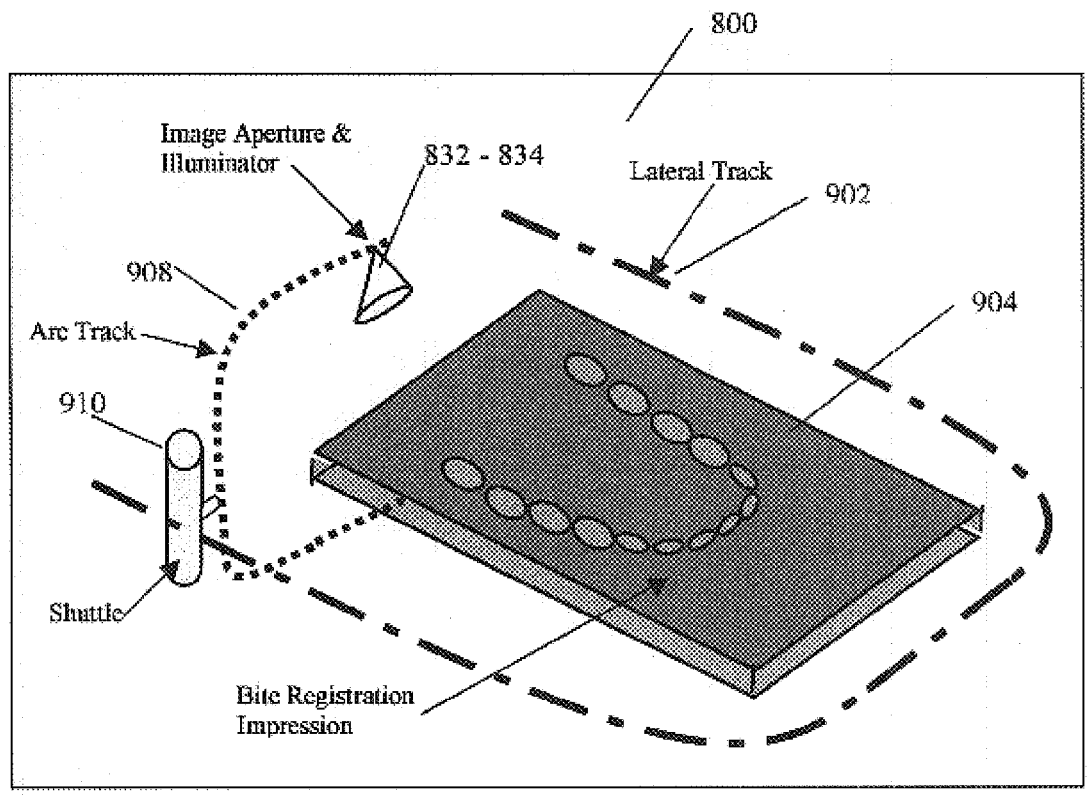
FIG. 9 shows an exemplary embodiment of a scanner with one movable image aperture.

The bite registration impression scanner 800 provides the mechanism for positioning the image aperture(s) 832 and the illuminator(s) 834 at known relative positions with respect to the bite registration impression while taking images of the bite registration impression surfaces. The scanner 800 in one embodiment includes a sensor arc track 908 that allows the image aperture to traverse an arc to capture the image of the both the upper and lower surfaces of the bite registration impression while also moving laterally (FIG. 9). In another embodiment, the scanner 800 supports multiple image gathering apertures in known mechanical alignment and moving of said apertures laterally around the bite registration impression (FIG. 10).

FIG. 9 shows one embodiment of the bite registration impression scan apparatus 800 having a single image aperture. In the embodiment of FIG. 9, the bite registration impression 904 is mounted within a lateral track 902 that is shaped substantially in an arch-shape or U-shape. The lateral track 902 supports a movable shuttle 910 driven by the drive mechanism 836. Attached to the shuttle 910 is an inwardly extending arc track arm 908, with the upper arm of the track extending above the upper surface of the mounted bite registration impression and the lower arm of the track extending below the lower surface of the mounted bite registration impression. Shown resting on top of the arc track arm 908 are the image aperture 832 and the illuminator 834 of FIG. 8. Additionally, the U-shaped lateral track 902 allows the shuttle 910 and arc track arm 908 to traverse laterally around the perimeter of the mounted bite registration impression 904. At each lateral position, the image aperture 832 and illuminator 834 traverses along the arc track arm 908 across the bite registration impression 904 surfaces to collect a sufficient number of images on both sides of the bite registration impression 904 before the shuttle 910 is moved to the next lateral position where the process is repeated. The lateral track 902 also includes sensors or indicators such as scale marks located at either end of the track 902 and along the track to provide image aperture 832 and illuminator 834 positional feedback information. Alternatively, positional information can be ascertained by methods such as counting drive motor revolutions and deducing the position based on counting motor revolutions.

Figure 10:
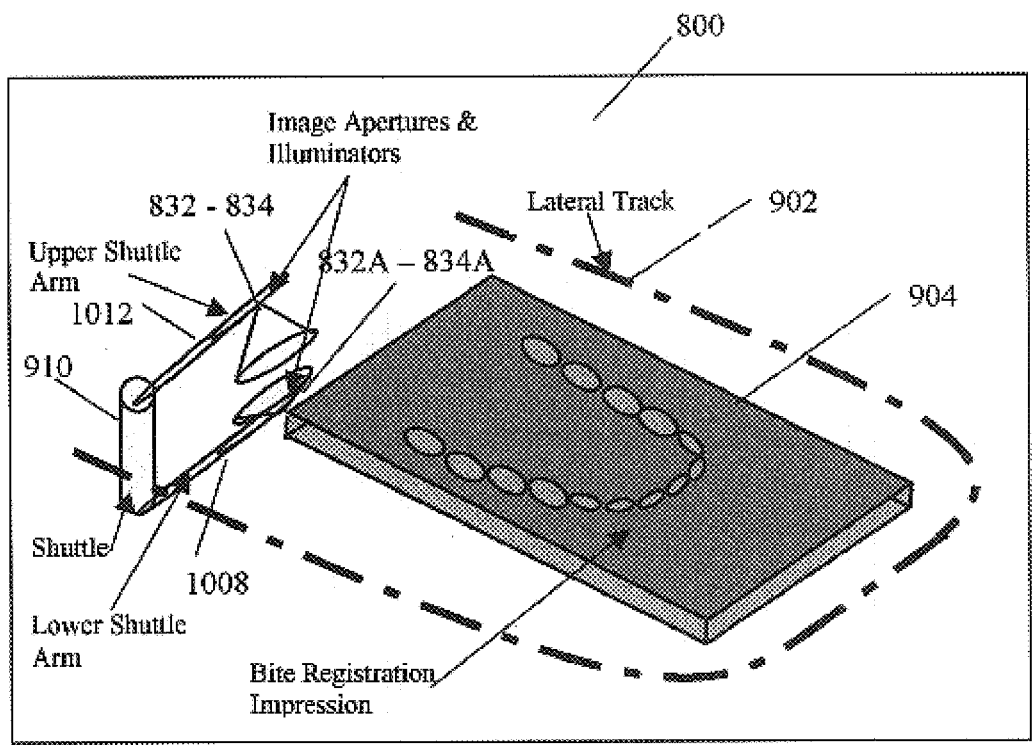
FIGS. 10 and 11 shows a second embodiment of a scanner with a plurality of movable image apertures, arranged in a manner such that both sides of the bite registration impression may be scanned simultaneously.
Figure 11:
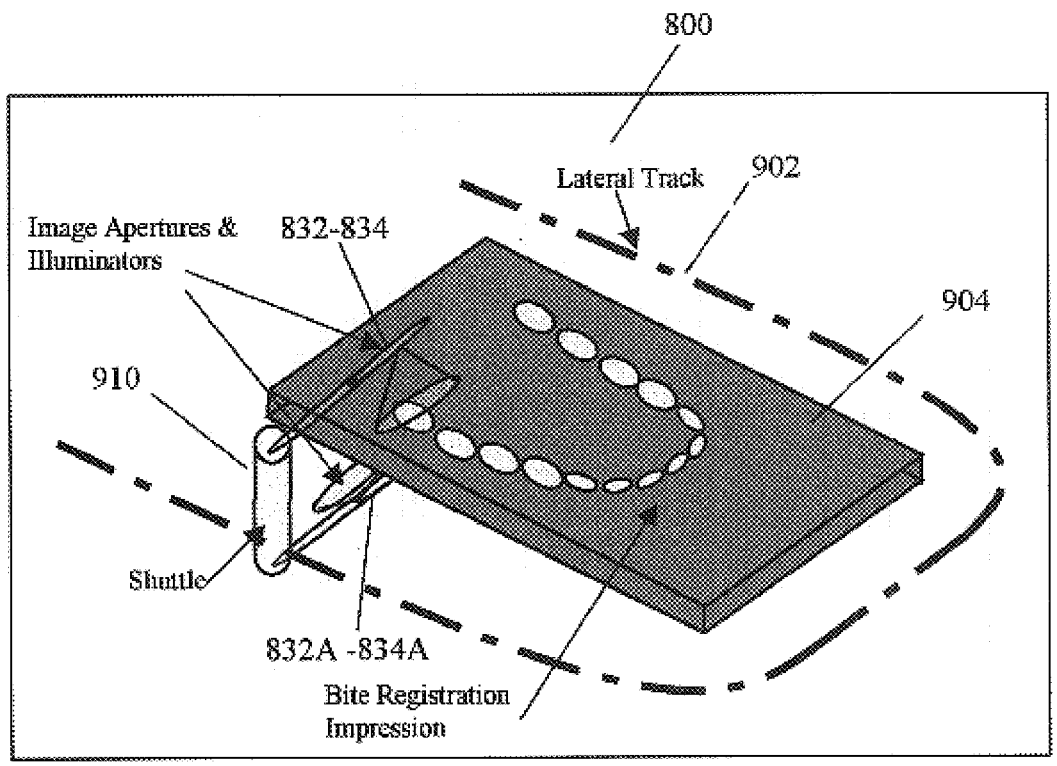

FIG. 10 shows another embodiment with multiple image apertures and illuminators that require only lateral motion. In this embodiment a plurality of image apertures 832–832A and the illuminators 834–834A are mounted in a known orientation to one another on an upper arm 1012 and a lower arm 1008 that are each attached to a laterally moveable shuttle 910 that traverses along track 902. FIG. 11 illustrates the case where the movable shuttle 910 has moved to a different lateral position along the track 902. At the shuttle position shown in FIG. 11, the upper image aperture 832 and illuminator 834 are imaging the upper surface of the bite registration impression 904, while at the same time the lower image aperture 832A and illuminator 834A are imaging the lower surface of the bite registration impression 904.

Figure 12:
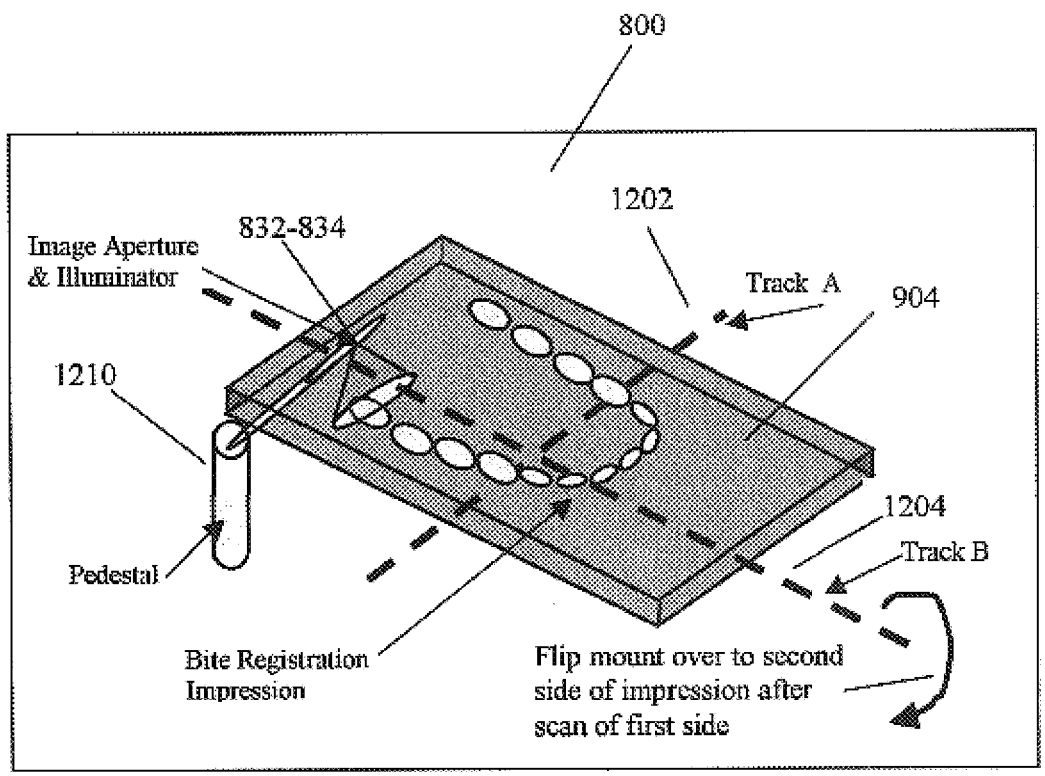
FIG. 12 shows a third embodiment of a scanner with a fixed image aperture and a movable mount for the bite registration impression.

The embodiments of the scanner described in FIGS. 9, 10 and 11 hold the bite registration impression fixed while one or more sets of image apertures and illuminators are moved in a manner to traverse across and image the upper and lower surfaces of the bite registration impression. FIG. 12 shows an alternative embodiment of this invention wherein an image aperture and illuminator are held in a fixed position while the bite registration impression is moved laterally and rotationally in a manner that results in the complete imaging of the upper and lower surfaces of the bite registration impression.

As shown in FIG. 12, the image aperture 832 and illuminator 834 are held in fixed position on a pedestal 1210 which is fixed to the base of the scanner 800. The mount 830 for the bite registration impression is movably attached to track A 1202 and track B 1204. The drive mechanism 836 sequentially moves the bite registration impression mount 830 in a manner that results in the imaging of the first surface of the bite registration impression 904. Upon completion of imaging the first surface of the bite registration impression, the drive mechanism 830 flips the bite registration mount over in a manner such that the second surface of the impression 904 is now facing towards the image aperture 832 and illuminator 834. Repeating the scan process, the drive mechanism 836 sequentially moves the bite registration impression mount 830 along track A 1202 and track B 1204 in a manner that results in the imaging of the second surface of the bite registration impression 904.

Figure 13:
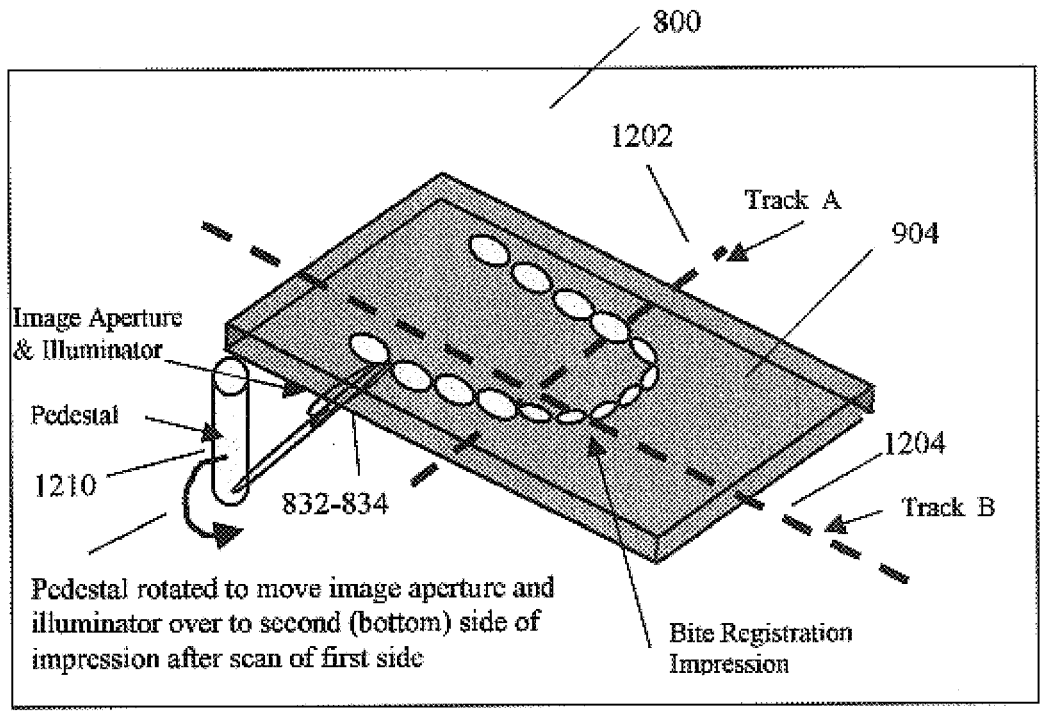
FIG. 13 shows a fourth embodiment of a scanner with a movable image aperture and a movable mount for the bite registration impression.

Alternatively, rather than flipping the bite registration mount 830 after the scan of the bite registration impression 904 first surface, the pedestal 1210 holding the image aperture 832 and illuminator 834 may be rotated as depicted in FIG. 13 to a new fixed position to provide image aperture visibility to the second surface of the bite registration impression 904. Another alternative embodiment (not shown) utilizes one or more fixed image apertures and illuminators positioned on each side of the bite registration impression such that, as the mount 830 is traversed along track A 1202 and track B 1204, both surfaces of the bite registration impression are being imaged at once.

The number of image apertures and their orientation is selected to provide sufficient coverage and overlap of the bite registration impression 904 upper and lower surface contours to be modeled at the desired resolution. At each imaging position, an image from each of the apertures 832 or 832A is recorded for later processing. In the embodiments of FIGS. 9, 10, 11, 12 and 13 the image apertures 832 or 832A may be sensors integral to the scanner 800 or optical image relay means such as gradient indexed lens or fiber optic image bundles may be connected directly to the image aperture. In the latter case, the gradient indexed lens or fiber optic image bundle transmits the image to the image sensor 810 on an external printed circuit board. To optimize the image collection at the image aperture, mirrored surfaces and optical lenses may be employed to direct and focus the image onto the image sensor.

As discussed above, the bite registration impression scanner 800 contains components that support one or more of the following functions: 1) illuminate the surfaces of the bite registration impression to be imaged; 2) digitally image the bite registration impression surfaces from different aspects; and 3) sequentially change the relative position of the illumination and imaging apertures with respect to the position of the bite registration impression surfaces so as to traverse across and image both the upper and lower bite registration impression surfaces.

Further, the output of the bite registration impression scanner 800 is received and processed by the image processor 810. In one embodiment, the output of the scanner 800 includes images transmitted through a fiber optic cable. These images are provided to a camera that digitizes the images and stores the digital images in a memory buffer. In a second embodiment, the output of the scanner 800 is already in digital form, and this data is stored in the memory buffer of the image processor 810 for processing, as described in more detail below.

Figure 14:
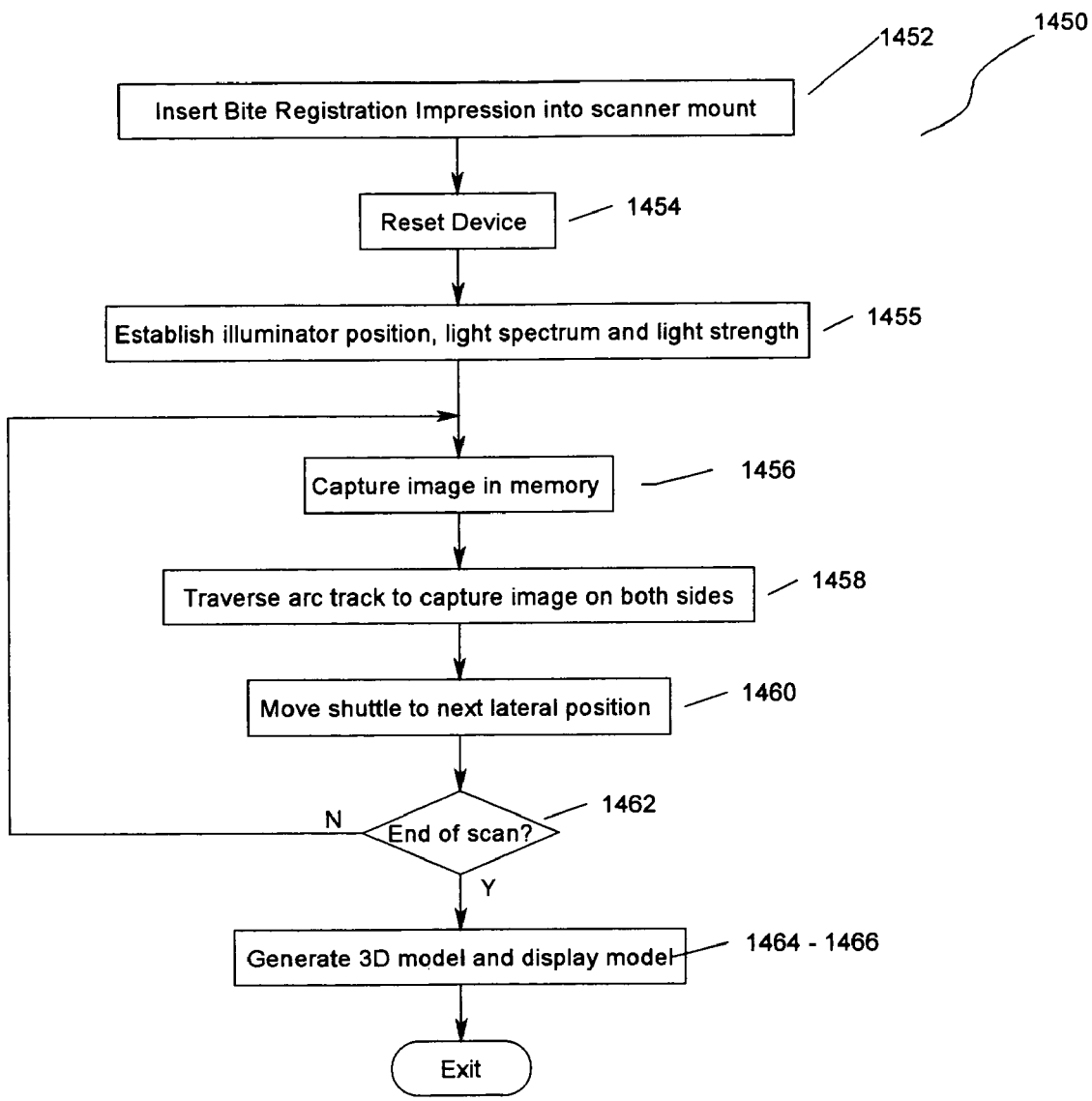
FIG. 14 illustrates a process for capturing images and developing 3D surface contour models of a bite registration impression.

FIG. 14 shows an exemplary process 1450 for scanning and generating 3D surface contour models of bite registration impressions based on the FIG. 9 embodiment of the invention. First, the bite registration impression 904 is inserted into the scanner 800 mount 830 (step 1452). Next, a reset operation is performed to establish a known relative position(s) of the image aperture(s) with respect to the bite registration impression surface(s) (step 1454). The illuminator 834 position, light spectrum and light strength is established (step 1455). The image processor 810 receives an image through the image aperture 832 and captures the image to its memory (step 1456). The image processor 810 then instructs the drive mechanism to move the image aperture along the arc track 908 to one or more additional known relative positions between the image aperture 832 and the bite registration impression 904 to collect a sufficient number of images on both sides of the impression (step 1458). Continuing to refer to the embodiment of FIG. 9, after obtaining the first set of images for the first shuttle position along the lateral track, the image processor 810 then actuates the drive mechanism 836 to move the shuttle 910 to the next incremental position along the lateral track 902 (step 1460). At each lateral position, the image aperture 832 traverses the arc track 908 over the bite registration impression 904 surfaces to collect a sufficient number of images on both sides of the impression before moving to the next lateral position. Next, the process 1450 tests whether the shuttle 910 reaches the end of the lateral track 902 (step 1462). If not, the process loops back to step 1456 to continue the image acquisition operation. If the end has been reached, the process 1450 generates a 3D surface contour model of the bite registration impression using the captured images (step 1464) and displays the 3D model for review (step 1466).

Figure 15:
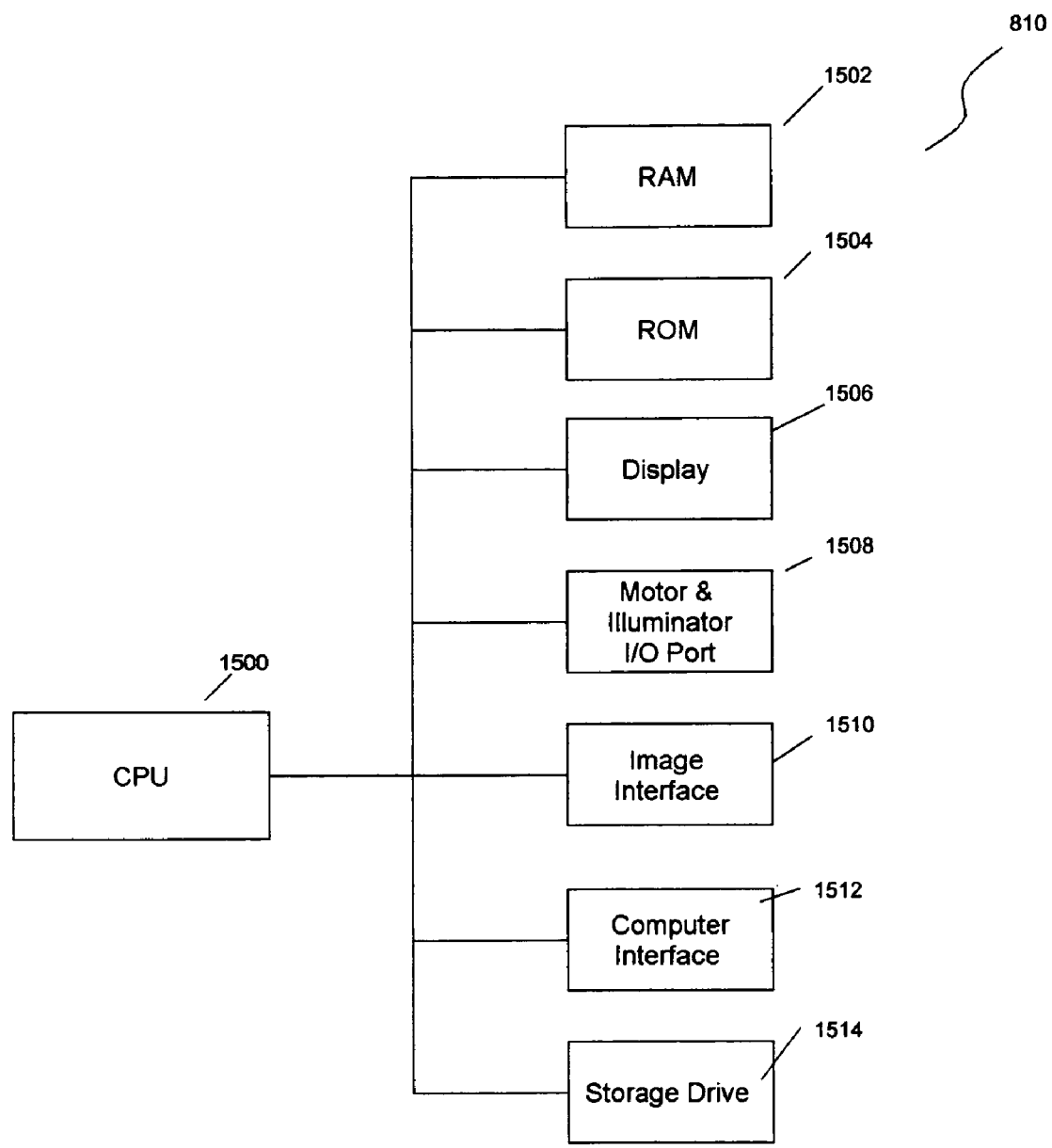
FIG. 15 shows an exemplary image processor for generating 3D models.

Turning now to FIG. 15, an exemplary image processor 810 is shown. The image processor 810 includes a central processing unit (CPU) 1500, which can be a high performance CISC or RISC processor. The CPU 1500 is connected to random access memory (RAM) 1502 and read only memory (ROM) 1504. The CPU 1500 also is connected to a plurality of input/output devices, including a display 1506, a motor and illuminator input/output port 1508 to control the drive mechanism 836 and the illuminator 834 (FIG. 8), an image interface 1510 to receive image data from the scanner 800, and a computer interface 1512. The CPU 1500 can also be connected to a storage drive 1514 such as a hard drive to store software and data and provides an interface for the communication of data with other equipment.

The CPU 1500 executes code to control the image data acquisition and generate 3D surface contour models from the captured images. The captured images are processed with a pattern recognizer that maps various points of an object observed in the captured images, thereby obtaining the shape/contour information. In one implementation, 2D digitized images of the bite registration impression surface are output from the scanner 800 and stored in computer memory of the image processor 810 along with the relative positional information and illuminator settings. The stored images from a plurality of images obtained at different known positions of the image aperture are then analyzed using stereometric methods to form a 3D view. This process is repeated for the complete set of captured images to create a full 3D surface contour model of the scanned surfaces of the bite registration impression. The 3D model is then presented on a display for review.

Figure 16:
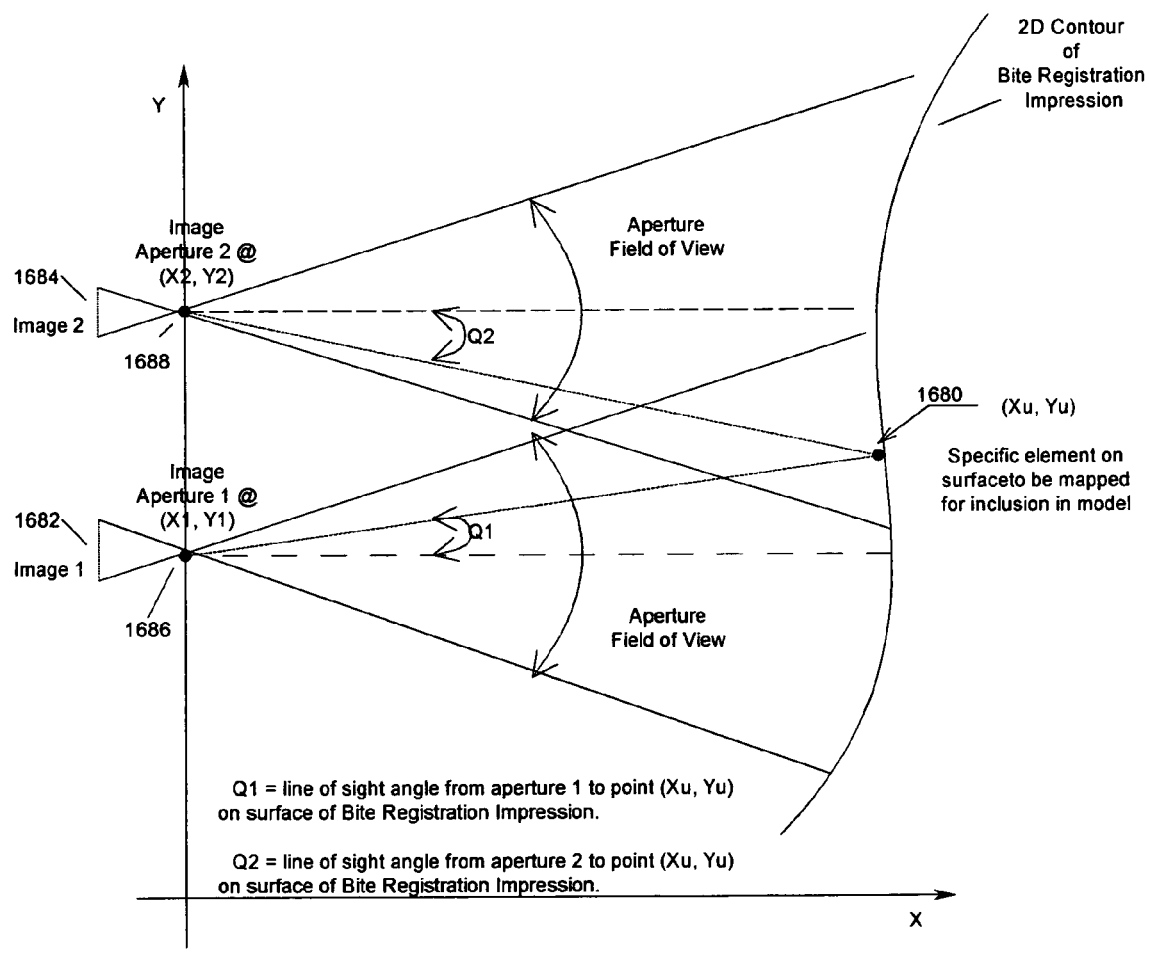
FIG. 16 shows an exemplary embodiment for modeling surface location and contour from stereo images.

FIG. 16 shows an exemplary embodiment for using stereo images to model the surface contour of a bite registration impression surface. The example of FIG. 16 is described in terms of two-dimensions, but the process is readily extended to the third axis to derive three-dimensional surface contours for 3D models. With reference to FIG. 16, the following process is used to derive the position of a specific scene element 1680 observed in images 1682 and 1684 captured through image apertures 1686 and 1688.

The image processor uses conventional image pattern matching techniques to identify a scene element that is observed in both image 1682 and image 1684. Further, based upon the image aperture field of view angle and the location of the specific scene element within the image sensor's array of pixels, the line of sight angle between the geometric plane of the image sensor and the scene element is derived. These line of sight angles are denoted in FIG. 16 as Q1 for an image aperture located at X1, Y1 and Q2 for an image aperture located at X2, Y2.

Let the as yet unknown coordinates for the location of the scene element of interest be denoted $x_u$ and $y_u$.

Based upon the geometry of the case of FIG. 16, $$y_u = (\tan Q1 \cdot x_u) + y_1$$

and $$\tan Q2 = (y_2 - y_u)/x_u$$

The value of $x_u$ and $y_u$ can now be solved using the above two equations and conventional techniques applicable to sets of linear equations. The stereometric method above can be generalized to add a third dimension $z_u$ and thereby derive a 3D surface contour model of the imaged bite registration impression surfaces. The 3D surface contour model is based on differences in the line of sight angles projected into the third dimension to a bite registration impression surface element as viewed from at least two different aperture locations.

While for illustrative purposes this description is based upon the use of just two images, it is to be understood that the concept can be extended to more precisely find the 3D coordinates of a scene element by utilizing a multitude of images of the bite registration impression surfaces, taken from a multitude of image aperture positions and utilizing a multitude of illumination conditions.

In another implementation, image-processing operations based on triangulation can be used where beams of light are projected onto the bite registration impression surfaces and three-dimensional spatial locations are determined for points where the light reflects from the surface. As the reflected light bounces off the bite registration impression surface at an angle relative to the known location and bearing of the light source, the system collects the reflection information from a known location relative to the light source and then determines the coordinates of the point or points of reflection by triangulation. A single dot system projects a single beam of light which, when reflected, produces a single dot of reflection. A scan line system beams a plane of light against the bite registration impression surface which is reflected as a curvilinear-shaped set of points describing one contour line of the imaged surface. The location of each point in that curvilinear set of points can be determined by triangulation. The system projects a light plane (i.e., a laser stripe) from a known location and reads the reflection of multiple points depicting the contour of the bite registration impression surface at a location distant from the camera and from which the position can be triangulated.

In addition to optical triangulation systems, other alternative optical scanning systems can be used, including range meter systems. Range meter systems typically use an infra-red-pulsed laser and mechanical scanning techniques to project a dot laser across an object and then measure the phase delay of the reflected signal.

Once the bite registration impression surface coordinates have been scanned, the system removes redundant points and generates a geometric 3D surface contour model from the scanned data using various techniques known in the art. In one embodiment, the process examines data for two adjacent laser stripes. Next, the process sweeps through each Y coordinate from the top of the two laser stripes to the bottom of the two stripes and creates triangles for the geometric 3D model. When the process has reached the bottom of the stripes, the triangulating process for the current laser stripes is finished and the next set of adjacent scan lines are retrieved until a triangulated mesh covering the bite registration impression surfaces is generated. Once the mesh has been generated, a 3D surface contour model with realistic shading and lighting can be generated.

Figure 17:
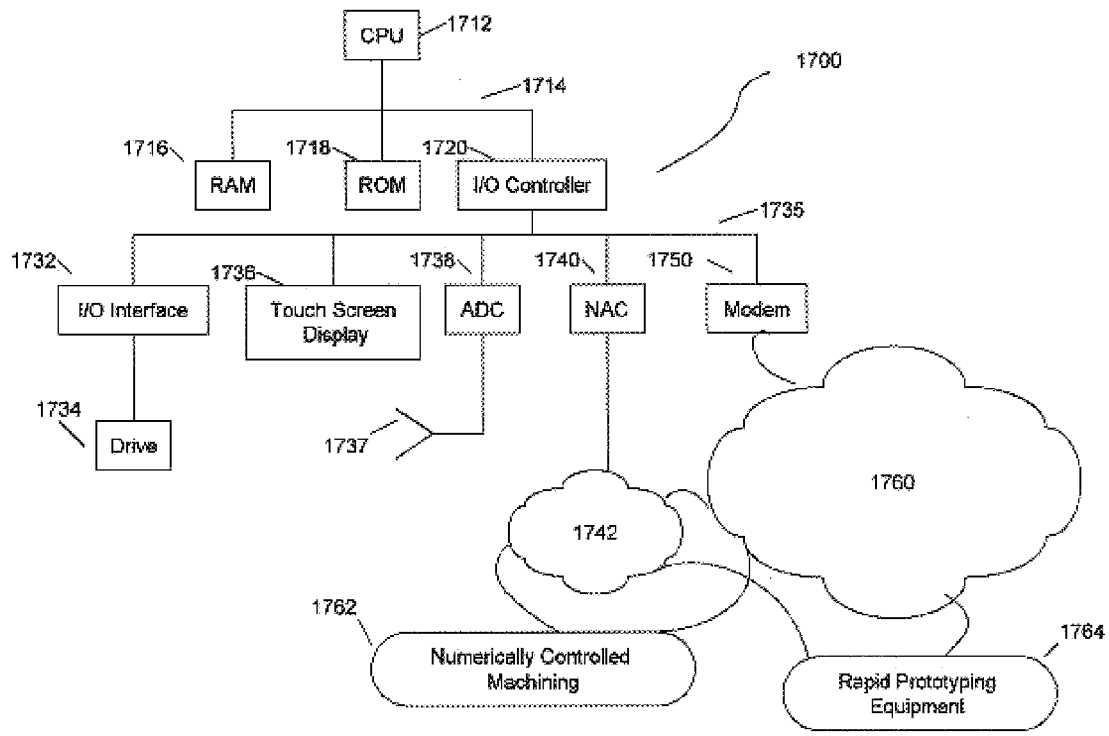
FIG. 17 shows an exemplary computer for using the 3D models.

FIG. 17 shows an exemplary computer 1700 for processing bite registration impression image processor data and for generating 3D surface contour models. The system 1700 includes a processor (CPU) 1712, RAM 1716, ROM 1718 and an I/O controller 1720 coupled by a CPU bus 1714. The I/O controller 1720 is also coupled to an I/O bus 1735. The I/O bus 1735 communicates with an I/O interface 1732 that in turn controls a solid state drive (flash RAM) 1734 or a removable disk drive. The I/O bus 1735 is also connected to input devices such as a touch-screen display 1736. In place of, or in parallel with the touch-screen display 1736, a keypad can be connected to the I/O bus 1735 to receive user data entry. Alternatively, voice recognition can be used, in conjunction with and/or replace the touch-screen display 1736 or keypad. In such an embodiment, a microphone 1737 is connected to an analog to digital converter (ADC) 1738 that interfaces with the processor 1712.

A network access card (NAC) 1740 can be connected to the I/O bus 1735 to allow the computer 1700 access to a network 1742. Through the network 1742, or through a modem 1750 connected to the I/O bus 1735, the computer 1700 can access a wide area network 1760 such as the Internet. An Internet community with one or more service providers or marketers is connected to the network. The transfer of bite registration impression 3D surface contour models to other equipment such as numerically controlled machining equipment 1762 or rapid prototyping equipment 1764 is supported by the system interfaces to the networks 1742 and 1760.

The above system supports a rapid imaging of dental bite registration impressions in such a way, and with sufficient resolution such that the acquired images can be processed into accurate 3D surface contour models of the imaged bite registration impressions. The images and models can be processed on the computer 1700 to provide dental diagnosis and to support the specification and manufacture of dental prosthetics such as bridgeworks, crowns or other precision moldings and fabrications.

Furthermore, the computer 1700 can transmit data representing a set of bite registration impression images or the corresponding 3D surface contour model over a local area network or a wide area network such as the Internet to a second location where a physical replicate of the bite registration impression 3D model can be fabricated. The replicate may be fabricated using numerically controlled machining equipment 1762 or rapid prototyping equipment 1764 that includes, but is not limited to, Stereo Lithographic Apparatus (SLA), Objet Polyjet (OBJ), Fused Deposition Modeling (FDM), Selective Laser Sintering (SLS) or Three Dimensional Printing (3DP) equipment. The physical replicate fabricated from the digital 3D surface contour model of the bite registration impression may be a full replicate or it may be a partial replicate of the original bite registration impression.

Figure 18:
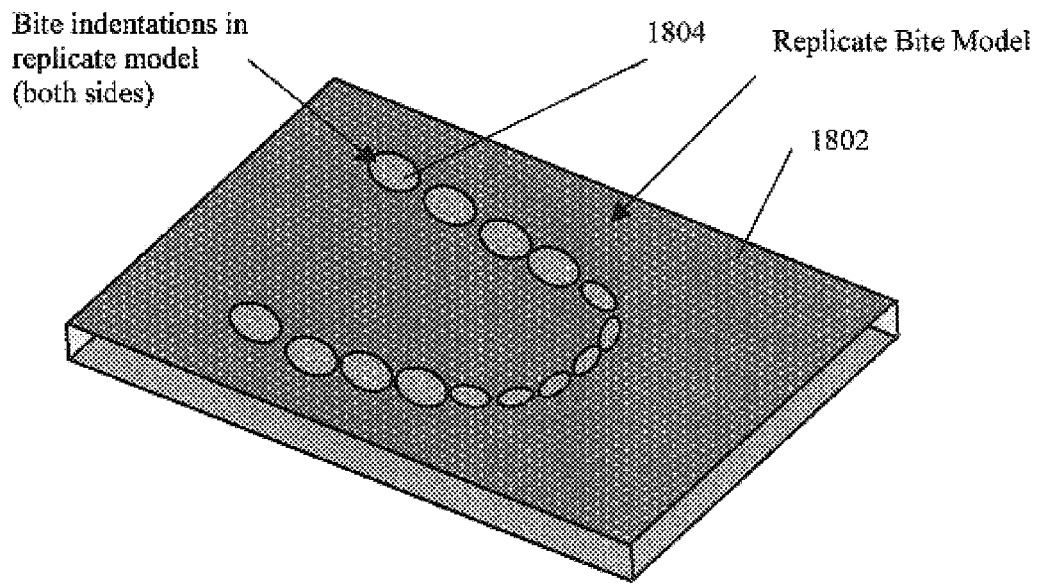
FIG. 18 shows an exemplary embodiment of a physical replicate of a bite registration impression made from the digital 3D surface contour model data and fabricated using numerically controlled machining or rapid prototype equipment such as Stereo Lithographic Apparatus (SLA), Objet Polyjet (OBJ), Fused Deposition Modeling (FDM), Selective Laser Sintering (SLS) or Three Dimensional Printing (3DP) equipment. This physical replicate is herein after referred to as the replicate bite registration impression model or replicate bite model, for short.

FIG. 18 depicts an exemplary result of fabricating a physical replicate of the bite registration impression from the 3D surface contour model of the impression. The replicate bite model 1802 duplicates the surface contours of the original bite registration impression and preserves and reflects the relative position and contours of the upper and lower jaw occlusal contact indentations 1804 obtained during the bite registration impression taking procedure in the dental office.

Figure 19:
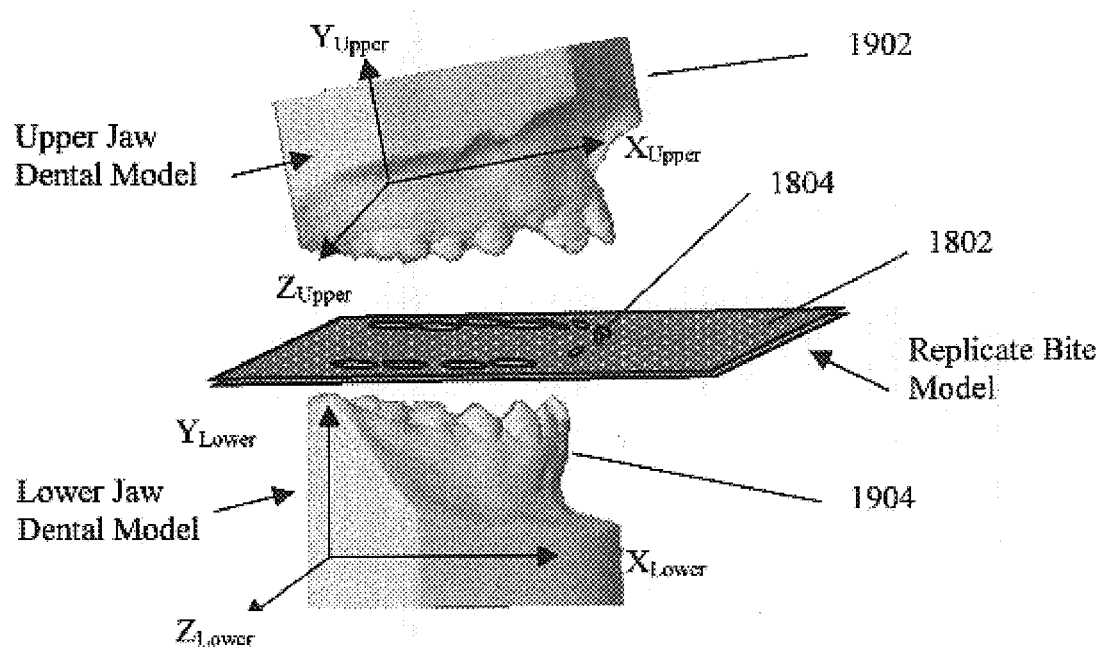
FIG. 19 illustrates the use of the replicate bite registration impression model to identify and correlate surface contour features in the replicate bite model with the corresponding features in the upper and lower jaw dental models.
Figure 20:
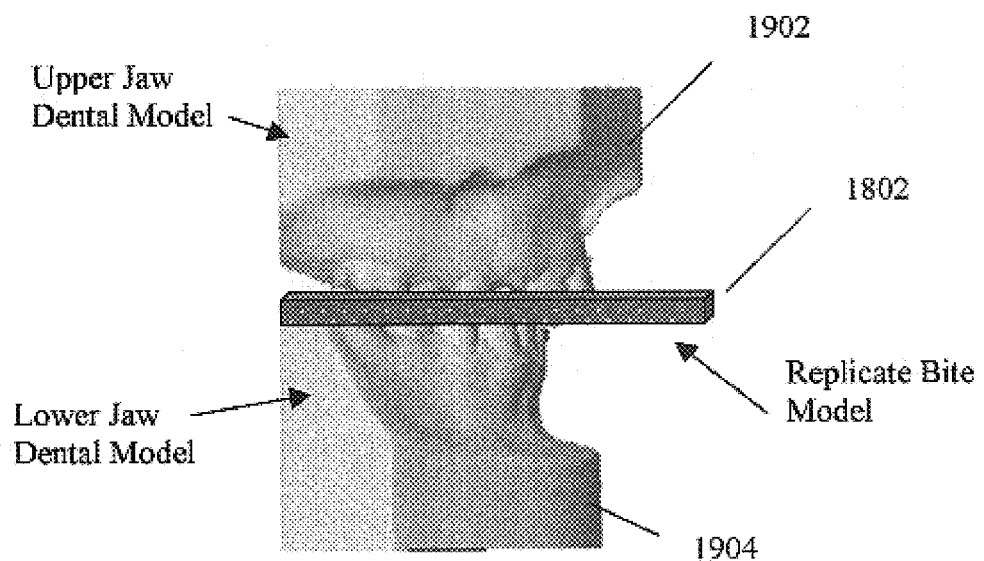
FIG. 20 illustrates the nesting of the upper and lower jaw dental models into the indentations in the replicate bite registration impression model and the consequential occlusal alignment of the upper and lower jaw dental models.

FIGS. 19 and 20 depicts the use of the replicate bite model to determine the proper occlusal alignment between a full or partial upper jaw dental model 1902 and a full or partial lower jaw dental model 1904. Initially, the occlusal alignment between the upper jaw dental model 1902 and the lower jaw dental model 1904 is unknown. As shown in FIG. 19 the alignment process begins by placing the replicate bite model 1802 between the opposing occlusal surfaces of the upper jaw dental model 1902 and the lower jaw dental model 1904. The replicate bite model 1802 and dental models are next moved and rotated with respect to each other until they are aligned such that the bite indentations in the replicate bite model corresponds with the features in the jaw models 1902–1904 that match the replicate bite model indentation characteristics. As depicted in FIG. 20, once the indentation features have been matched, the upper jaw model 1902 is nested into the corresponding indentations in the first surface of the replicate bite model 1802 and the lower jaw model 1904 is similarly nested into its corresponding indentations in the second surface of the replicate bite model 1802.

The occlusal alignment of the upper jaw dental model 1902 with the lower jaw dental model 1904 is now complete and may be directly viewed by the dentist or the dental laboratory technician. To facilitate future viewing of the alignment between the jaw dental models, corresponding marks or surfaces may be placed on the upper and lower jaw models or the jaw models may be mounted in an dental articulation jig. After installation in the articulator jig, the proper alignment of the upper and lower jaw dental models may be rechecked using the replicate bite model.

Although an illustrative embodiment of the present invention, and various modifications thereof, have been described in detail herein with reference to the accompanying drawings, it is to be understood that the invention is not limited to this precise embodiment and the described modifications, and that various changes and further modifications may be effected therein by one skilled in the art without departing from the scope or spirit of the invention as defined in the appended claims.

What is claimed is:

1. A method for determining the occlusal alignment of jaw dental models using a physical replicate of an occlusal bite registration impression, comprising:
    a) creating a digital 3D surface contour model of the bite registration impression;
    b) fabricating a physical replicate bite model of the bite registration impression using the data from the digital 3D surface contour model of the bite registration impression;
    c) correlating features on the upper and lower jaw dental models with features on the replicate bite model; and
    d) aligning the occlusal contact of the upper jaw and lower jaw dental models by nesting the upper jaw dental model occlusal features into the corresponding features in the replicate bite model features and nesting the lower jaw dental model occlusal features into its corresponding features in the replicate bite model.

2. The method of claim 1, wherein the bite registration impression is used to show a partial occlusion.

3. The method of claim 1, wherein the bite registration impression is used to show a full occlusion.

4. The method of claim 1, wherein the dental models represent partial jaws.

5. The method of claim 1, wherein the dental models represent full jaws.

6. The method of claim 1, wherein the replicate bite model represents a full bite registration impression.

7. The method of claim 1, wherein the replicate bite model represents a partial bite registration impression.

8. The method of claim 1, wherein the replicate bite model is fabricated using numerically controlled machining equipment.

9. The method of claim 1, wherein the replicate bite model is fabricated using rapid prototyping equipment.

10. The method of claim 9, wherein the replicate bite model is fabricated using stereo lithographic apparatus (SLA) rapid prototyping equipment.

11. A system for determining the occlusal alignment of jaw dental models using a replicate of an occlusal bite registration impression, comprising:
    a) means for imaging the surface of the bite registration impression;
    b) means for using the image data to create a digital 3D surface contour model of the bite registration impression;
    c) means to fabricate a physical replicate bite model from the data file for the digital 3D surface contour model of the bite registration impression; and
    d) means for using the replicate bite model to align the occlusal surfaces of the upper jaw and lower jaw dental models.

12. The system of claim 11, wherein the bite registration impression is used to show a partial occlusion.

13. The system of claim 11, wherein the bite registration impression is used to show a full occlusion.

14. The system of claim 11, wherein the dental models represent partial jaws.

15. The system of claim 11, wherein the dental models represent full jaws.

16. The system of claim 11, wherein the replicate bite model represents a full bite registration impression.

17. The system of claim 11, wherein the replicate bite model represents a partial bite registration impression.

18. The system of claim 11, wherein the replicate bite model is fabricated using numerically controlled machining equipment.

19. The system of claim 11, wherein the replicate bite model is fabricated using rapid prototyping equipment.

20. The system of claim 19, wherein the replicate bite model is fabricated using stereo lithographic apparatus (SLA) rapid prototyping equipment.

* * * * *